United States Patent
Zhao

(10) Patent No.: US 9,010,958 B2
(45) Date of Patent: Apr. 21, 2015

(54) PENETRATING ILLUMINATOR FOR VEIN OBSERVATION

(71) Applicant: Dezheng Zhao, Qingdao (CN)

(72) Inventor: Dezheng Zhao, Qingdao (CN)

(73) Assignee: China Qingdao Medical Manufacturing, Co., Ltd., Qingdao, Shandong (CN)

( * ) Notice: Subject to any disclaimer, the term of this patent is extended or adjusted under 35 U.S.C. 154(b) by 270 days.

(21) Appl. No.: 13/622,685

(22) Filed: Sep. 19, 2012

(65) Prior Publication Data
US 2013/0114249 A1    May 9, 2013

(30) Foreign Application Priority Data

Nov. 7, 2011 (CN) ............ 2011 2 0436113 U
May 24, 2012 (CN) ............ 2012 2 0235700 U

(51) Int. Cl.
*F21L 4/00*    (2006.01)
*A61B 5/00*    (2006.01)

(52) U.S. Cl.
CPC ............ *A61B 5/0059* (2013.01); *A61B 5/489* (2013.01)

(58) Field of Classification Search
CPC ............................ A61B 5/0059; A61B 5/489
USPC .......................... 362/183, 157, 190
See application file for complete search history.

(56) References Cited

U.S. PATENT DOCUMENTS

| 2003/0016532 | A1 | 1/2003 | Reed |
| 2005/0168980 | A1* | 8/2005 | Dryden et al. ............... 362/230 |
| 2010/0256455 | A1* | 10/2010 | Hsia et al. ................... 600/249 |
| 2011/0125028 | A1 | 5/2011 | Wood et al. |

FOREIGN PATENT DOCUMENTS

| EP | 0 435 500 A1 | 7/1991 |
| EP | 1 555 476 A2 | 7/2005 |
| WO | 2009070815 A2 | 6/2009 |

OTHER PUBLICATIONS

The extended European Search Report issued on Mar. 15, 2013 by the European Patent Office in corresponding European Patent Application No. 12180764.8-1660. (6 pages).

* cited by examiner

*Primary Examiner* — David V Bruce
(74) *Attorney, Agent, or Firm* — Buchanan Ingersoll & Rooney PC

(57) ABSTRACT

A penetrating illuminator for vein observation, including a case, a lens and a light hole in the upper case, a circuit board in the case, a power source and an LED lamp. The case includes an upper part and a lower part; the rims of the upper case and lower case are in the shape of a circular arc while the top of the upper case is made into the shape of an arc protruding from the center. The lower case is rear-connected to a handle at an obtuse angle. Configured as a child's hand, it is especially suitable for use on children. Simply place the hand, with palm down, over the illuminator emitting penetrating light. A fixing stand is provided, including a base plate and a rod in the center of the base plate, wherein a groove is provided to accept the handle.

15 Claims, 2 Drawing Sheets

PENETRATING ILLUMINATOR FOR VEIN OBSERVATION

FIELD OF THE INVENTION

The disclosure relates to a penetrating illuminator for vein observation during surgical operations, or to be specific, a type of illuminator that can penetrate the human body to show the veins for the convenience of surgical operations.

BACKGROUND OF THE INVENTION

At present, veins are usually spotted with the naked eye for intravenous injection and surgical operation. The veins in the back of the hand (or in the arms, legs, insteps, etc) are so thin that it is difficult to find them. Sometimes several attempts are required to get the needle in place, causing excessive pain to the patient. In some cases, treatments or operations are delayed due to the difficulty in spotting the veins. The present disclosure is made to help solve this problem, and it is especially suitable for child patients. The LED rays from the illuminator can penetrate the hand, providing a clear picture of the veins. For example, the "Vein Illumination Device for Piercing" is a utility model patent (No.200620104185.1) granted to this applicant, which comprises a case with a light hole on the top, wherein a bulb in the case at the light hole is used as the light source, which is controlled by a switch on the case together with the battery. The rays from the bulb can penetrate the hand to show clearly the veins for the purpose of intravenous injection, etc. The said invention features a square cubic shape, with a short handle, which is not very convenient for use and unsuitable for use on children.

This disclosure is made to solve the problems by reforming the overall shape of the device to make it more convenient and fit for children.

SUMMARY

In order to solve the problems in the existing devices, this disclosure discloses a type of illuminating apparatus that is more convenient and suitable for children.

According to one embodiment, an illuminating apparatus comprises a case, a lens in the light hole in the top of the case, a circuit board, a power source, and an LED lamp in the case. The case includes an upper part and a lower part; the rims of the upper case and lower case are in the shape of a circular arc while the top of the upper case is made into the shape of a vault; the hole and lens are in the upper case, and the lower case is rear-connected to a handle; the angle between the bottom plane of the lower case and the axis of the handle is an obtuse angle.

Modifications that may be made to the embodiment include the handle is hollow with a battery box for the said power source inside it; there is a fixture block in the handle, and the box cover which is part of the handle snap-fits with the fixture block.

Further modifications to the embodiment: a groove is provided inside the handle to accommodate the fingers of the user.

Further modifications to the embodiment: a circuit board with an LED lamp is installed in the lower case; and a convex lens with a condenser is provided for the LED lamp.

Further modifications to the embodiment: a switch is provided in the circuit board, with an opening at the inside-back of the upper and lower cases, from which the switch is exposed.

Further modifications to the embodiment: a stand comprising a base plate and a rod is provided in the center of the base plate, with a groove at the end of the base plate for the handle, and a fixing plate tilting to the rod at the groove.

Further modifications to the embodiment: a hollow handle is provided, with a box for rechargeable battery inside the handle; the power source is a rechargeable battery which is in the battery box; the battery box has a cover which snap-fits with the handle and becomes part of it; a recharging socket at the bottom of the handle, which is connected to the rechargeable battery via cables.

Further modifications to the embodiment: a stand with a recharging function is provided, with a plug in the groove in the base plate of the stand, and a socket for recharging cables at the back of the stand. The plug in the stand is connected to the socket via cables.

Further modifications to the embodiment: a smooth slope is provided on top of the rod in touch with the handle, the fixing plate is in the shape of a semicircle arc, and the inside of the fixing plate agrees with the back of the handle.

Further modifications to the embodiment: a switch is provided on the circuit board, with an opening at where the forefinger is placed on the handle at the lower case, from which the switch is exposed.

Further modifications to the embodiment: USB interfaces are provided for both the recharging socket and power socket, and the recharging plug is compatible with the USB interfaces.

Further modifications to the embodiment: a disposable sanitary film covers the top of the upper case to prevent cross-infection, the film is a degradable disposable transparent septum membrane.

Further modifications to the embodiment: the switch is a regulating switch and a light control circuit on the circuit board is connected to the LED lamp. Through the regulating switch and the light control circuit, power is supplied to the LED lamp. With the switch, the LED lamp can be easily regulated via the light control circuit according to actual needs.

Advantages and Positive Effects of the Disclosure

This disclosure is realized by changing the existing type of vein observation lamp, which is square cubic shaped and has a short handle, into one with circular arc rims in the upper and lower cases and an uprising vault at the top of the upper case to suit to children's hands. The handle connected to the back of the lower case, and the angle between the bottom plane of the lower case and the axis of the handle is an obtuse angle, which renders the device more convenient to use.

One embodiment uses a hollow handle to provide space for the power source, thus reducing the size of the device and making it more suitable for use on children.

This embodiment makes it more convenient for the user to switch on and off the light, with reduced light irritation to the eyes.

This embodiment makes it convenient for the user to fix it in a certain position.

While holding this embodiment, the user can use the thumb to hold the back of the patient's hand for secured insertion of the needle, etc.

This device has a stand, and the bottom of the handle can be inserted into a groove at one end of the base plate and fastened by a fixing plate at the groove, and the handle is supported in the middle by a rod in the center of the base plate; this design makes the device secure and convenient for the user to perform operations.

One embodiment has a hollow handle to include the rechargeable battery as the power source; there is a cover for the battery box, which snap-fits with the handle and becomes part of it; the rechargeable battery is durable, with reduced cost and environmental pollution; the stand of this device has recharging function, with a plug in the groove in the base plate of the stand for recharging the battery and a socket at the back of the stand; the plug in the stand is connected to the power socket via cables; the plug can be connected to the power socket at the bottom of the handle to recharge the battery. The stand of the new design reduces costs and facilitates use and storage.

A disposable film covers the top of this device, where the patient's hand is placed, for easy replacement after each use and avoidance of cross-infection, The film is a degradable disposable transparent septum membrane, to prevent the pollution of the environment.

This device is simple in structure, and easy to fabricate, with great commercial potential.

The switch on the circuit board of this device is a regulating switch, with which the LED lamp can be easily regulated according to actual needs.

Where:

1. upper case; 2. lens; 3. condenser; 4. LED lamp; 5. lower case; 5-1. handle 6. switch; 7. fixture block; 8. box cover; 9. battery box; 10. rechargeable battery; 11. recharging module; 12. rod; 13. base plate 14. cable for Recharging battery; 15. fixing plate

DETAILED DESCRIPTION OF THE PREFERRED EMBODIMENTS

To show the purpose, technical scheme and advantages of an embodiment of this invention, an explicit and complete statement of the technical proposal is made based on the figures contained herein. The embodiments described hereunder are prima face some of the embodiments of this invention, which should not be construed as all the embodiments. Any other embodiment based on the embodiment of this invention by ordinary technicians in this field without innovative work shall be exclusively covered by the patent of this invention.

Figure 1:
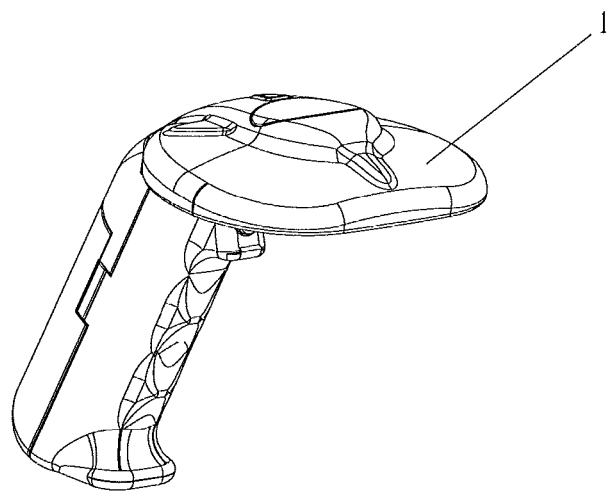
FIG. 1 is a perspective view of an embodiment of this invention.
Figure 2:
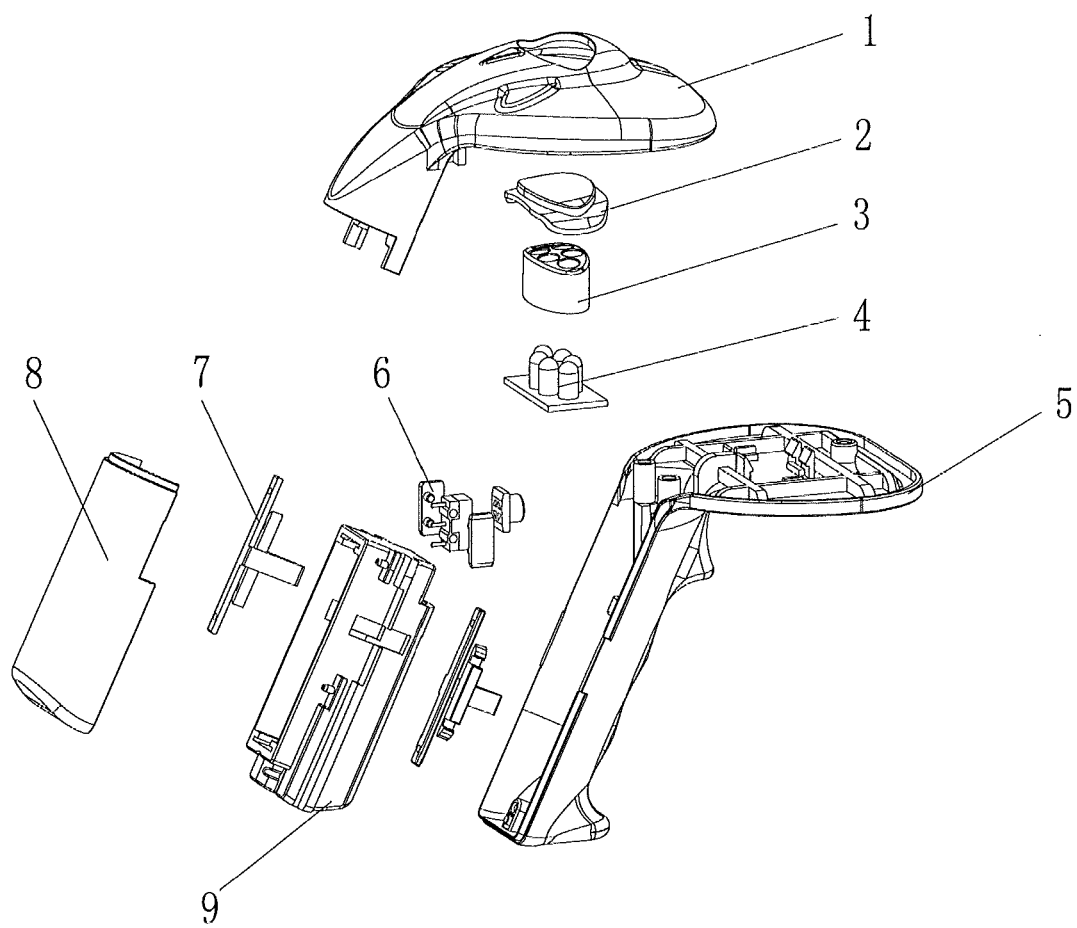
FIG. 2 is an assembly drawing of an embodiment of this invention.

FIG. 1 and FIG. 2 show the embodiments of this invention, comprising a case, lens 2 in the hole at the top of the case, circuit board in the case, a power source and LED lamp 4.

This embodiment is a modification to the existing vein lamp in a square cubic shape with a short handle. The case of the embodiment includes an upper case 1 and a lower case 5, and the rims of the upper case 1 and lower case 5 are designed into a circular arc, while the top of the upper case 1 is a rising vault; the light hole and the lens 2 are mounted on upper case 1. There is a circuit board on the lower case 5, and an LED lamp 4 is mounted on the circuit board; there is condenser 3 around the LED lamp 4, and the lens 2 is a convex lens. The lower case 5 is connected to a handle, and the angle between the bottom plane of the lower case and the axis of the handle is at an obtuse angle, or to be specific, an angle of about 100°-150°.

The handle is hollow, and the battery box 9 for the power source is in the cavity. There is a fixture block 7 in the handle, which fastens box cover 8 on battery box 9 to close battery box 9. Box cover 8 is part of the handle which has finger groove at the inside for convenient holding of the invention by medical staff.

There is a switch 6 in the circuit board, and an opening at the inside-back of the upper case 1 and lower case 5; the switch 6 is exposed through the opening at the inside-back of the upper case 1 and lower case 5 to the outside.

When using this device, overhead fluorescent lights, if any, should preferably be switched off to avoid light interference, and low-power non-fluorescent side lights should be used. The LED lamp should shed light from the palm towards the hand back. The user should hold the handle of the device with one hand, using the thumb to hold down the patient's hand, and use another hand to perform injection operations. The vein at the back of the patient's hand can be easily seen. The small round case makes it easier to move by the user, especially suitable to children's hands.

This device can also be used for intravenous injection in the feet, arms and legs of children.

Figure 3:
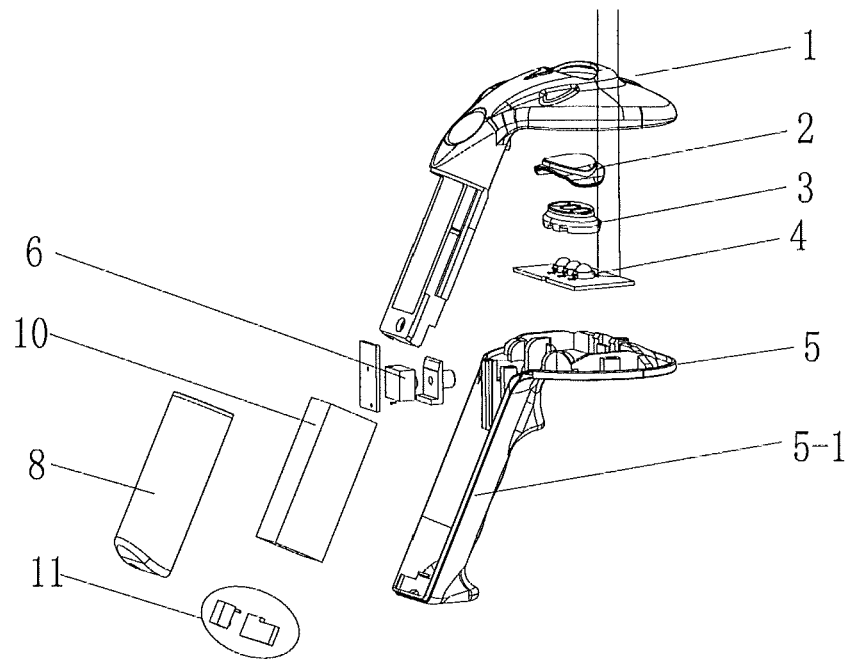
FIG. 3 is an assembly drawing of an embodiment of this invention with a rechargeable battery.
Figure 4:
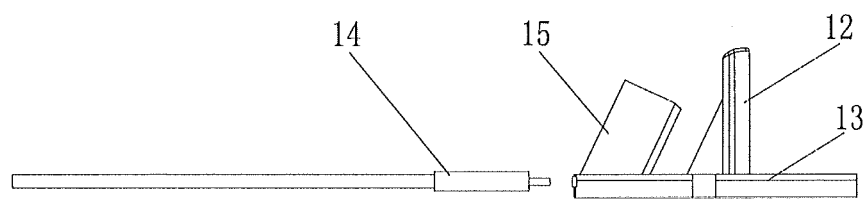
FIG. 4 is an illustration of a recharging stand and cables of an embodiment of this invention.
Figure 5:
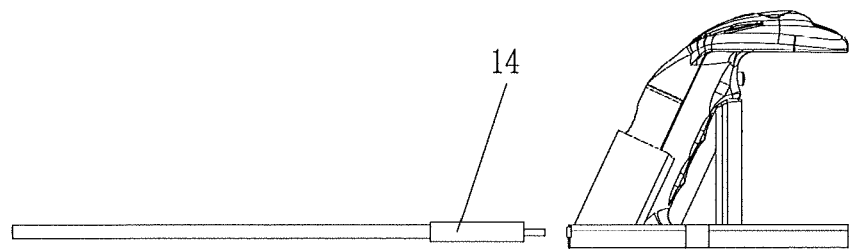
FIG. 5 is an illustration of an embodiment of this invention ready for recharging the battery.

FIGS. 3-5 are embodiments of the rechargeable unit, which is fundamentally similar to the aforementioned embodiment except for the modifications to the handle. Handle 5-1 below lower case 5 in this embodiment is a hollow one, with a battery box for rechargeable battery 10 in the cavity. The power source is a rechargeable battery 1, which is contained in the battery box; there is cover 8 for the battery box, which is part of handle 5-1 and is fastened to handle 5-1. There is a module 11 at the bottom of the handle 5-1, which includes a recharging socket and a circuit board; the recharging socket can be connected to rechargeable battery 10 via the circuit board and cables, and the recharging socket is fitted on the bottom of the said handle 5-1.

There is a switch 6 on the circuit board with an LED lamp 4, and there is an opening in the handle of the lower case 5-1 where the finger of the user is placed; the switch 6 is exposed from the opening.

There is a stand on the aforesaid two embodiments of the device. The stand includes a base plate 13 and a rod 12 at the center of base plate 13. There is a groove at one end of the base plate 13 for fixing the handle of the device, and there is a fixing plate 15 around the groove tilting toward the rod 12. The top of the rod 12 in touch with the handle is a smooth slope, the fixing plate 15 is a semicircle arc plate, and the inside face of fixing plate 15 basically conforms to the back of the handle.

The stand of this device also has a recharging function. Besides the fixing function, it can be used to recharge the device using a rechargeable battery. There is a plug for recharging in the groove in stand base plate 13, and there is a recharging socket at the back of base plate 13; the plug in the stand base plate 13 is connected to the recharging socket via cables. In addition, there is a cable 14 for recharging the battery.

The connections of the cable 14 and the power socket on the bottom of handle 5-1 can be connected to USB interfaces, and the recharging plug at base plate 13 and the plug at one end of cable 14 can be inserted into USB ports.

When recharging is required, put the device in the groove of the stand, and the recharging plug in the groove is connected to the socket at the bottom of handle 5-1 to recharge battery 3 in handle 5-1. The plug at one end of recharging cable 14 is connected to the socket at the back of base plate 13, and the other end is connected to the power socket. Where the stand is not wanted in a recharging process, just connect the plug at one end of recharging cable 14 to the socket at the bottom of handle 5-1, and the other end of cable 14 to the power socket.

The top of upper case 1 of the device, where the patient's hand is placed, is covered by a piece of film, with a shape preferably matching the top of case 1 but slightly larger. The film is a degradable disposable transparent septum membrane through which light can pass. The film may be changed after each use.

Switch 6 of the device is a regulating switch, and a light control circuit is connected to LED lamp 4. Through regulating switch 6 and the said light control circuit, power is supplied to LED lamp 4.

Scheme 1: The light control circuit is a regulating resistor. Through regulating switch 6 and the light control circuit, power is supplied to LED lamp 4 to realize continuously variable control of LED lamp 4.

Scheme 2: The light control circuit is formed by three resistors of different values in parallel. Through regulating switch 6 and the light control circuit, power is supplied to LED lamp 4 to realize 3-step control of LED lamp 4.

With the regulating switch and the light control circuit, the LED lamp can be easily regulated for clearer observation of blood vessels in patient's hand.

The aforementioned embodiments are only ideal ones under this invention, which do not constitute any limitation to the application of this invention. Technicians in this field may modify or improve the embodiments based on the aforementioned technical disclosure to come up with their equivalents. However, any other embodiment based on the technical disclosure of this invention with only simple modifications, or equivalent variation or remodeling shall be exclusively covered by the patent of this invention.

What is claimed is:

1. A penetrating illuminator for vein observation, comprising:
    a case which includes an upper part and a lower part;
    a hole in the upper part of the case;
    a lens fitted in the hole in the upper part of the case;
    a circuit board in the case;
    a handle to which the lower part of the case is connected;
    a power source; and
    an LED lamp;
    wherein rims of the upper part of the case and the lower part of the case are in a shape of a circular arc, while a top of the upper case is an uprising arc, and
    wherein the handle projects from the lower part of the case, away from the upper part of the case, at an obtuse angle between a bottom plane of the lower part of the case and an axis of the handle.

2. The illuminator of claim 1, wherein the handle is hollow and is provided with a battery box for the power source, and a fixture block, which snap-fits with a box cover, which is part of the handle.

3. The illuminator of claim 1, wherein a groove is provided inside the handle to accommodate fingers of a user.

4. The illuminator of claim 1, wherein a circuit board with an LED lamp is provided in the lower case; and a convex lens with a condenser is provided for the LED lamp.

5. The illuminator of claim 1, wherein a switch is provided on the circuit board, with an opening at an inside of said upper or lower cases, from which the switch is exposed.

6. The illuminator of claim 5, wherein the switch is a regulating switch and a light control circuit on the circuit board is connected to the LED lamp, through the regulating switch and the light control circuit, power is supplied to the LED lamp.

7. The illuminator of claim 1, further comprising a stand comprising a base plate and a rod in a center of the base plate, with a groove for the handle at one end of the base plate, and a fixing plate tilting to the rod at the groove.

8. The illuminator of claim 7, wherein a stand with recharging function is provided, with a plug in the groove in the base plate of the stand, and a socket for recharging cables at the back of the stand, the plug in the stand is connected to the socket via cables.

9. The illuminator of claim 7, wherein a smooth slope is provided on top of the rod in touch with the handle, the fixing plate is in the shape of a semicircle arc, and the inside of the fixing plate fits with the back of the said handle.

10. The illuminator of claim 8, wherein a smooth slope is provided on top of the rod in touch with the handle, the fixing plate is in the shape of a semicircle arc, and the inside of the fixing plate agrees with the back of the handle.

11. The illuminator of claim 7, wherein a switch is provided on the circuit board, with an opening at where the forefinger is placed on the handle at the lower case, from which the switch is exposed.

12. The illuminator of claim 10, wherein USB interfaces are provided for both the recharging socket and power socket, and the recharging plug is compatible with USB interfaces.

13. The illuminator of claim 11, wherein the switch is a regulating switch and a light control circuit on the circuit board is connected to the LED lamp, through the regulating switch and the light control circuit, power is supplied to the LED lamp.

14. A penetrating illuminator for vein observation, comprising:
    a case which includes an upper part and a lower part;
    a hole in the upper part of the case;
    a lens fitted in the hole in the upper part of the case;
    a circuit board in the case;
    a handle to which the lower part of the case is connected;
    a power source; and
    an LED lamp;
    wherein rims of the upper part of the case and the lower part of the case are in a shape of a circular arc, while a top of the upper case is an uprising arc, and
    wherein the handle projects from the lower part of the case, at an obtuse angle between a bottom plane of the lower part of the case and an axis of the handle,
    wherein the handle is hollow and is provided with a box for a rechargeable battery;
    the power source is a rechargeable battery which is contained in the box;
    a cover of the box snap-fits with the handle and becomes part of it; and
    there is a recharging socket at the bottom of the handle, and the recharging socket is connected to the rechargeable battery via cables.

15. A penetrating illuminator for vein observation, comprising:
    a case which includes an upper part and a lower part;
    a hole in the upper part of the case;
    a lens fitted in the hole in the upper part of the case;
    a circuit board in the case;
    a handle to which the lower part of the case is connected;
    a power source; and
    an LED lamp;

wherein rims of the upper part of the case and the lower part of the case are in a shape of a circular arc, while a top of the upper case is an uprising arc, and wherein the handle projects from the lower part of the case, at an obtuse angle between a bottom plane of the lower part of the case and an axis of the handle, wherein a disposable sanitary film covers the top of the upper case, the film is a degradable disposable transparent septum membrane.

* * * * *